United States Patent [19]

Bosshard et al.

[11] 4,020,067
[45] Apr. 26, 1977

[54] TRIAZINYL-AMIDINES

[75] Inventors: René Bosshard, Birsfelden; Hans U. Brechbühler, Basel, both of Switzerland

[73] Assignee: Ciba-Geigy Corporation, Ardsley, N.Y.

[22] Filed: Sept. 10, 1975

[21] Appl. No.: 612,125

[30] Foreign Application Priority Data

Sept. 12, 1974 Switzerland .................... 12418/74
Aug. 15, 1975 Switzerland .................... 10661/75

[52] U.S. Cl. ..................... 260/249.6; 260/249.8; 424/249
[51] Int. Cl.² ....................... C07D 251/66
[58] Field of Search .................... 260/249.6

[56] References Cited

UNITED STATES PATENTS 3,879,338  4/1975  Varsanyi et al. ............... 260/249.6

FOREIGN PATENTS OR APPLICATIONS 1,339,393  11/1962  France

Primary Examiner—John M. Ford
Attorney, Agent, or Firm—Harry Falber

[57] ABSTRACT

New triazinylamidines of the formula

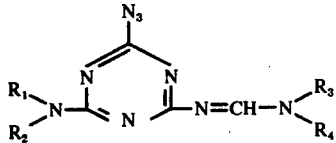

wherein
$R_1$ represents a hydrogen atom or a $C_1$–$C_4$-alkyl radical, and
$R_2$ represents a $C_1$–$C_4$-alkyl, $C_3$–$C_6$-cycloalkyl, $C_3$–$C_4$-alkenyl, $C_3$–$C_5$-alkynyl or methoxy-($C_1$–$C_4$)-alkyl radical, or $R_1$ and $R_2$ together with the N atom represent a heterocyclic ring, and
$R_3$ and $R_4$ each represent a methyl or ethyl radical, compositions containing these compounds as active ingredients and use of these compositions for the control of parasitic pests.

15 Claims, No Drawings

TRIAZINYL-AMIDINES

The present invention relates to new triazinylamidines which have an action on pests, to processes for producing these amidines, as well as to compositions and processes for the control of pests by use of the new amidines as active substances.

The new triazinylamidines of the invention correspond to the formula I

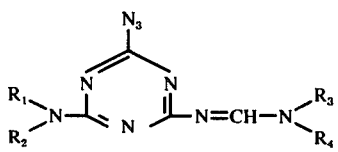

wherein
- $R_1$ represent a hydrogen atom or a $C_1$–$C_4$-alkyl radical, and
- $R_2$ represents a $C_1$–$C_4$-alkyl, $C_3$–$C_6$-cycloalkyl, $C_3$–$C_4$-alkenyl, $C_3$–$C_5$-alkynyl or methoxy-($C_1$–$C_4$)-alkyl radical, or $R_1$ and $R_2$ together with the N atom represent a heterocyclic ring, and
- $R_3$ and $R_4$ each represent a methyl or ethyl radical.

Alkyl, alkenyl and alkynyl radicals in the formula I can be branched-chain or straight-chain. Alkyl radicals denoted by $R_1$ and $R_2$ are methyl, ethyl, n-propyl, isopropyl, n-butyl, isobutyl, sec.butyl and tert.butyl radicals. Such alkyl radicals form also the alkyl moieties of methoxyalkyl substituents. To be mentioned as alkenyl or alkynyl radicals are, e.g., allyl, methallyl and propargyl. By cycloalkyl radicals are meant the cyclobutyl, cyclopentyl and cyclohexyl and, in particular, the cyclopropyl radical.

Triazinylamidines of the above-mentioned formula I of particular importance on account of their action on pests, especially on insects and on weeds, are those wherein
- $R_1$ represents a hydrogen atom or a methyl or ethyl radical,
- $R_2$ represents a methyl, ethyl, isopropyl, cyclopropyl or propargyl radical, or $R_1$ and $R_2$ together with the adjacent nitrogen atom represent a pyrrolidino radical, and
- $R_3$ and $R_4$ each represent a methyl or ethyl radical;

and preferred triazinylamidines among these are those wherein
- $R_1$ and $R_2$ both represent a methyl radical or both an ethyl radical, or wherein
- $R_1$ represents a hydrogen atom, and
- $R_2$ represents a methyl, ethyl, isopropyl, cyclopropyl or propargyl radical, and wherein
- $R_3$ and $R_4$ each represent a methyl or ethyl radical.

The new compounds of the formula I are advantageously produced by methods known per se; for example, by a process wherein a. an azido-bis-amino-triazine derivative of the formula II

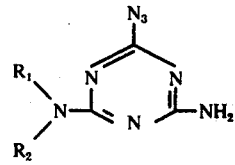

is reacted with a carboxylic acid amide-acetal or carboxylic acid amide-ketal of the formula III

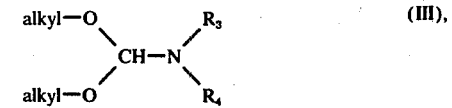

or b. a triazine derivative of the formula IV

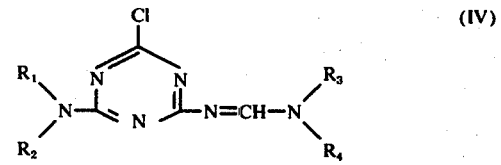

is reacted with an alkali metal azide, preferably in the presence of a quaternised base, or is reacted with hydrazine and the resulting hydrazino-s-triazine of the formula V

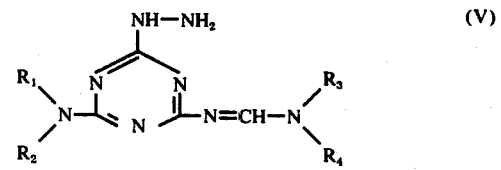

is reacted with an alkali metal nitrite.

In the formulae II to V above, the substituents $R_1$, $R_2$, $R_3$ and $R_4$ have the meanings given already under the formula I, while "alkyl" stands for a $C_1$–$C_5$-alkyl radical. The reaction (a) is preferably performed in a solvent or diluent that is inert to the reactants; for example, in aliphatic or aromatic hydrocarbons such as benzene, toluene or xylenes; halogenated hydrocarbons such as chlorobenzene, chloroform or methylene chloride; ethers and ethereal compounds such as dialkyl ether, dioxane or tetrahydrofuran; ketones such as acetone or methyl ethyl ketone; nitriles such as acetonitrile, etc.; as well as in mixtures of such solvents. Catalysts, such as p-toluene-sulphonic acid, can be added to the reaction mixture, but are not absolutely necessary. The reaction temperature is between 30° and 130° C. The derivatives of the formula II used as starting materials are obtainable from the corresponding, already known, chloro-bis-amino-s-triazine compounds of the formula VI

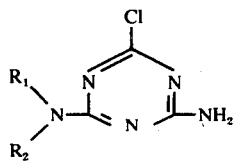

(VI)

e.g. by reaction with alkali metal azide, preferably in the presence of a quaternising base. Suitable bases for process (b) are, in particular, tertiary amines such as trialkylamines. Water or acetone is preferably used as solvent or diluent for the reaction. The starting materials of the formula IV can be produced by a procedure analogous to that in the case of process (a) from the corresponding chloro-bis-amino-S-triazine compound of the above-mentioned formula VI.

The new compounds of the formula I are suitable for the control of pests, especially for the control of insects, e.g. of the order Diptera.

In contrast to conventional insecticides which, as contact or stomach poisons, kill or cripple the insects in several hours, the active substances of the formula I affect above all the development of the larvae. The action results in dying off of the egg larvae or in prevention of the emergence of adjust insects from the pupae.

Active substances of the formula I are harmless for warm-blooded animals, and can accordingly be used in veterinary preparations, e.g. for the control of pests on animals of commercial value or as feed additives.

Furthermore, a number of the new triazinylamidines possess herbicidal and plant-growth-regulating properties.

The compounds of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

solid preparations: dusts, scattering agents, granulates, coated granulates, impregnated granulates and homogeneous granulates and premix (feed additive);

liquid preparations:
a. water-dispersible active-substance concentrates: wettable powders, pastes or emulsions;
b. solutions: aerosols.

The solid preparations (dusts or scattering agents) are produced by mixing the active substances with solid carriers. Suitable carriers are, for example, kaolin, talcum, loess, chalk, limestone, ground limestone, attapulgite, dolomite, diatomaceous earth, precipitated silicic acid, alkaline-earth silicates sodium and potassium aluminium silicates (feldspars and mica), secondary calcium phosphate, calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Granulates can be very easily produced by dissolving an active substance of the formula I in an organic solvent, and applying the solution obtained to a granulated mineral, e.g. attapulgite, $SiO_2$, granicalcium, bentonite, etc., and then evaporating off the organic solvent.

Granulates are obtained, e.g., by compacting the carrier material with the active substances and additives and subsequently reducing the compacted material to small pieces.

It is possible to add to these mixtures also additives stabilising the active substance, and/or nonionic, anion-active and cation-active substances which improve, for example, the adhesiveness of the active substances (adhesives and agglutinants), and or ensure better wettability (wetting agents) as well as dispersibility (dispersing agents).

Suitable substances are, for example; the following: olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, lignin-sulphonic acid, the alkali metal salts and alkaline-earth metal salts thereof, polyethylene glycol ethers (carbowaxes), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones polyvinyl alcohols, condensation products of urea and formaldehyde, as well as latex products.

Water-dispersible concentrates of active substances, i.e. wettable powders, pastes and emulsion concentrates, are agents which can be diluted with water to obtain any desired concentration. They consist of active substance, carrier, optionally additives stabilising the active substance, surface-active substances and anti-foaming agents and, optionally, solvents.

The wettable powders and pastes are obtained by the mixing and grinding of the active substances with dispersing agents and pulverulent carriers, in suitable devices, until homogeneity is obtained. Suitable carriers are, e.g., those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali metal salts, ammonium salts and alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary acetylene glycols, dialkyl dilauryl ammonium chloride and fatty acid alkali-metal salts and alkaline-earth metal salts.

Suitable anti-foaming agents are, e.g., silicones.

The active substances are so mixed, ground, sieved and strained with the above-mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g., alcohols, xylenes, toluene, dimethylsulphoxide and mineral oil fractions boiling in the range of 120° to 350° C. The solvents must be non-phytotoxic, and inert to the active substances.

Furthermore, the compositions according to the invention can be used in the form of solutions. For this purpose the active substance, or several active substances, of the general formula I is, or are, dissolved in suitable organic solvents, solvent mixtures or water. As organic solvents, it is possible to use aliphatic and aromatic hydrocarbons, their chlorinated derivatives, alkylnaphthalenes, mineral oils on their own or in admixture with each other.

The content of active substance in the above-described compositions is between 0.1 and 95%.

Other biocidal active substances or agents can be mixed with the described compositions of the invention. For the broadening of their sphere of action, the new compositions can contain, in addition to the stated compounds of the general formula I, for example insecticides, fungicides, bactericides, fungistatics, bacteriostatics or nematocides. The compositions of the invention may also contain fertilisers, trace elements, etc..

The active substances of the formula I can be formulated, for example, as follows (parts signify parts by weight):

Spray

The following constituents are used to produce (a) a 5% spray and (b) a 2% spray:
a. 5 parts of active substance,
1 part of epichlorohydrin,
94 parts of petrol (boiling limits 160°–190° C);
b. 2 parts of active substance,
1 part of diazinone,
97 parts of kerosene.

Dusts

The following substances are used to produce (a) a 0.5% dust and (b) a 2% dust:
a. 0.5 part of active substance,
99.5 parts of talcum;
b. 2 parts of active substance,
1 part of highly dispersed silicic acid,
97 parts of talcum.
The active substances are mixed and ground with the carriers.

Scattering Agent 5 parts of active substance are mixed with
95 parts of calcium carbonate,
and the mixture is ground to a mean particle size of 80 μ.

Granulate 5 parts of active substance are dissolved in a solvent such as methylene chloride, and the solution is mixed with
2 parts of polyethylene glycol ("Carbowax"). With this mixture there are impregnated
91.5 parts of calcium carbonate, and
1.5 parts of precipitated silicic acid are mixed in, and the solvent is subsequently evaporated off.

Bait Granulate 2.0 parts of active substance,
0.05 part of a dyestuff, and
1.0 part of Celite or kaolin are mixed and finely ground.
96.85 parts of crystallised sugar are mixed together with the above mixture, and the whole is impregnated with
0.1 part of an adhesive dissolved in, e.g., a small amount of isopropanol, and the solvent is evaporated off.

Wettable Powder.

50 parts of active substance are mixed and finely ground with
5 parts of dispersing agent, e.g. sodium lignin sulphonate,
5 parts of a wetting agent, e.g. dibutyl-naphthalene sulphonate,
10 parts of silicic acid and
30 parts of kaolin.

Premix (Feed Additive)

0.25 part of active substance and
4.75 parts of secondary calcium phosphate, or kaolin, aerosil or calcium carbonate are homogeneously mixed with
95.00 parts of an animal feed such as, e.g. rabbit feed.

Emulsifiable Concentrates

The following substances are used to produce (a) a 10%, (b) a 25% and (c) a 50% emulsifiable concentrate:
a. 10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;
b. 25 parts of active substance,
2.5 parts of epoxidised vegetable oil,
10 parts of alkylarylsulphonate/fatty alcohol polyglycol ether mixture,
5 parts of dimethylformamide,
57.5 parts of xylene;
c. 50 parts of active substance,
4.2 parts of tributylphenol-polyglycol ether,
5.8 parts of calcium-dodecylbenzenesulphonate,
20 parts of cyclohexanone,
20 parts of xylene.

It is possible to prepare from these concentrates, by dilution with water, emulsions of any desired concentration.

The following examples serve to further illustrate the invention. The temperature values relate to degrees Centigrade.

EXAMPLE 1

Production of
N²-(2-ethylamino-4-azido-s-triazinyl-(6))-N',N'-dimethylformamidine of the formula (Compound No. 1)

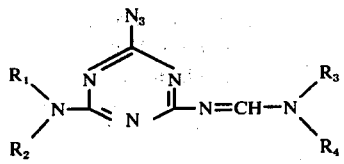

(Ia):

| Comp. No. | $R_1$ | $R_2$ | $R_3$ | $R_4$ | m.p. |
|---|---|---|---|---|---|
| 2 | $C_2H_5-$ | $C_2H_5-$ | $CH_3-$ | $CH_3-$ | 146–147° C |
| 3 | H— | ▷— | $CH_3-$ | $CH_3-$ | 125–127° C |
| 4 | H— | $CH_3\backslash CH{-} / CH_3$ | $CH_3-$ | $CH_3-$ | 144–145° C |
| 5 | $CH_3-$ | $CH_3-$ | $CH_3-$ | $CH_3-$ | 147–148° C |
| 6 | H— | $CH\equiv C-CH_2-$ | $CH_3-$ | $CH_3-$ | 188–189° C (decomp.) |
| 7 | H— | $CH_3-$ | $CH_3-$ | $CH_3-$ | 187–190° C |
| 8 | H— | $CH\equiv C-C(CH_3)_2-$ | $CH_3-$ | $CH_3-$ | 147–149° C |
| 9 | H— | $CH_3-$ | $C_2H_5-$ | $C_2H_5-$ |  |
| 10 | H— | $CH_3\backslash CH{-} / CH_3$ | $C_2H_5-$ | $C_2H_5-$ | 112–118° C |
| 11 | H— | $C_2H_5-$ | $C_2H_5-$ | $C_2H_5-$ |  |
| 12 | H— | $CH_3-C(CH_3)_2-$ (with $CH_3$) | $C_2H_5-$ | $C_2H_5-$ | 122–123° C |
| 13 | H— | $CH_2=CH-CH_2-$ | $CH_3-$ | $CH_3-$ | 154–156° C |
| 14 | H— | $CH_3OCH_2CH_2CH_2-$ | $CH_3-$ | $CH_3-$ | 98–103° C |
| 15 | H | (cyclohexyl)-C≡CH | $CH_3-$ | $CH_3-$ | 130–132° C |
| 16 | $C_2H_5$ | $C_2H_5$ | $C_2H_5$ | $C_2H_5$ | 65–67° C |
| 17 | H | $CH_3-CH_2-CH_2-$ | $CH_3-$ | $CH_3-$ | 149–150° C(decomp.) |
| 18 |  | —N(pyrrolidinyl) | $CH_3-$ | $CH_3-$ | 149–153° C |
| 19 | H | n-propyl | $CH_3-$ | $CH_3-$ | 149–150° C |

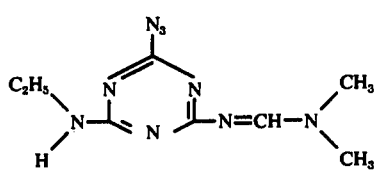

16 g of 2-amino-4-azido-6-ethylamino-s-triazine is mixed with 200 ml of benzene, and 21 g of N,N-dimethylformamide-dimethylacetal with 0.3 g of p-toluenesulphonic acid (as catalyst) are added. The reaction mixture is refluxed for about 4 hours at 80° C, during which time everything becomes dissolved. As a result of cooling with ice and addition of an amount of hexane, the product precipitates out in solid form. The product (Compound No. 1) is filtered off and recrystallised from isopropanol: m.p. 163°–164° C.

The following compounds of the formula Ia are produced analogously:

EXAMPLE 2

Insecticidal Action

Action against *Musca domestica*

An amount in each case of 50 g of CSMA*maggot substrate was weighed off in beakers. For each active substance, 2.5 ml of a 1% acetonic solution of the respective substance was transferred by pipet twice to 50 g of maggot substrate each time. After a thorough mixing of the treated substrate, the solvent was allowed to evaporate off. There was then deposited per active substance in each case 25 1-, 2- and 3-day-old maggots and about 50 fly eggs. After completion of pupation, the pupae were flushed out and counted. After a period of 10 days, the number of emerged flies was counted and hence any effect on metamorphosis was established.

*Chemical Specialities Manufacturers Association

The compounds of the preceding Example 1 have in this test a favourable inhibitory effect. Compounds 1 to 5 are to be emphasised on account of their particularly good action.

EXAMPLE 3

Action against Lucilia sericata

To 9 ml of a culture medium there is added at 50° C 1 ml of an aqueous solution containing 0.5% of active substance. There are then transferred to the culture medium about 30 freshly emerged Lucilia sericata larvae, and the insecticidal action is determined after 48 and 96 hours by an assessment of the mortality rate.

The compounds of the formula I exhibit in this test a good action against Lucilia sericata.

EXAMPLE 4

Insecticidal Action against Aedes aegypti

Onto the surface of 150 ml of water in a container there is transferred by pipette specific amounts of a 0.1% acetonic solution of the active substance to obtain concentrations of 10.5 and 1 ppm, respectively. After the acetone has been evaporated off, there are placed into each of the respective containers 30–40 2-day-old Aedes larvae. The mortality is determined after 1,2 and 5 days.

The compounds according to Example 1 exhibit in this test a good action against Aedes Aegypti.

We claim:

1. A compound of the formula I

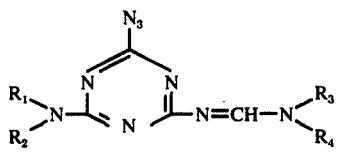

wherein
  $R_1$ represents a hydrogen atom or a $C_1$–$C_4$-alkyl radical, and
  $R_2$ represents a $C_1$–$C_4$-alkyl, $C_3$–$C_6$- cycloalkyl, $C_3$–$C_4$-alkenyl, $C_3$–$C_5$-alkynyl or methoxy ($C_1$–$C_4$)-alkyl radical, or $R_1$ and $R_2$ together with the N atom represent a pyrrolidino radical, and
  $R_3$ and $R_4$ each represent methyl or ethyl.

2. The compound according to claim 1 wherein in formula I
  $R_1$ represents a hydrogen atom or a methyl or ethyl radical,
  $R_2$ represents a methyl, ethyl, isopropyl, cyclopropyl or propargyl radical, or $R_1$ and $R_2$ together with the adjacent nitrogen atom represents a pyrrolidino radical, and
  $R_3$ and $R_4$ each represent a methyl or ethyl radical.

3. The compound according to claim 2 wherein in the formula I
  $R_1$ and $R_2$ both represent a methyl radical or both an ethyl radical, and
  $R_3$ and $R_4$ each represent a methyl or ethyl radical.

4. The compound according to claim 2 wherein in the formula I
  $R_1$ represents a hydrogen atom,
  $R_2$ represents a methyl, ethyl, isopropyl, cyclopropyl or propargyl radical, and
  $R_3$ and $R_4$ each represent a methyl or ethyl radical.

5. $N^2$-(2-Ethylamino-4-azido-s-triazinyl-(6))-$N'$,$N'$-dimethylformamidine according to claim 1.

6. $N^2$-(2-Diethylamino-4-azido-s-triazinyl-(6))-$N'$,$N'$-dimethylformamidine according to claim 1.

7. $N^2$-Cyclopropylamino-4-azido-s-triazinyl-(6)-$N'$,$N'$-dimethylformamidine according to claim 1.

8. $N^2$-(2-Isopropylamino-4-azido-s-triazinyl-(6))-$N'$,$N'$-dimethylformamidine according to claim 1.

9. $N^2$-(2-Dimethylamino-4-azido-s-triazinyl-(6))-$N'$,$N'$-dimethylformamidine according to claim 1.

10. An insecticidal composition which contains as active substance an insecticidally effective amount of a triazinyl-amidine of the formula I

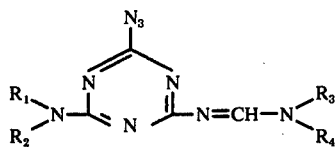

wherein
  $R_1$ represents a hydrogen atom or a $C_1$–$C_4$-alkyl radical, and
  $R_2$ represents a $C_1$–$C_4$-alkyl, $C_3$–$C_6$-cycloalkyl, $C_3$–$C_4$-alkenyl, $C_3$–$C_5$-alkynyl or methoxy-($C_1$–$C_4$)-alkyl radical, or $R_1$ and $R_2$ together with the N atom represent a pyrrolidino radical, and
  $R_3$ and $R_4$ each represent methyl or ethyl according to claim 1 together with a suitable carriers therefor.

11. A method of combatting insects which comprises applying to the locus thereof an insecticidally effective amount of a triazinyl-amidine of the formula I

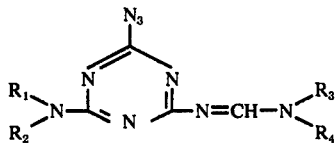

wherein
  $R_1$ represents a hydrogen atom or a $C_1$–$C_4$-alkyl radical, and
  $R_2$ represents a $C_1$–$C_4$-alkyl, $C_3$–$C_6$-cycloalkyl, $C_3$–$C_4$-alkenyl, $C_3$–$C_5$-alkynyl or methoxy-($C_1$–$C_4$)-alkyl radical, or $R_1$ and $R_2$ together with the N atom represent a pyrrolidino radical, and
  $R_3$ and $R_4$ each represent methyl or ethyl, according to claim 1.

12. Process according to claim 11 for combatting insects of the order Diptera.

13. The process of claim 11, wherein $R_1$ represents a hydrogen atom or a methyl or ethyl radical, $R_2$ represents a methyl, ethyl, isopropyl, cyclopropyl or propargyl radical, or $R_1$ and $R_2$ together with the adjacent nitrogen atom represents a pyrrolidino radical, and $R_3$ and $R_4$ each represent a methyl or ethyl radical.

14. The process of claim 11, wherein $R_1$ and $R_2$ both represent a methyl radical or both an ethyl radical, and $R_3$ and $R_4$ each represent a methyl or ethyl radical.

15. The process of claim 11, wherein $R_1$ represents a hydrogen atom, $R_2$ represents a methyl, ethyl, isopropyl, cyclopropyl or propargyl radical, and $R_3$ and $R_4$ each represent a methyl or ethyl radical.

* * * * *